United States Patent [19]

Schwartz et al.

[11] Patent Number: 4,810,507

[45] Date of Patent: Mar. 7, 1989

[54] PRODUCTION OF FERMENTED VEGETABLE OIL PRODUCTS CONTAINING AN EMULSIFIER

[75] Inventors: Robert D. Schwartz, Concord; Thomas M. Anderson, Emeryville; Enrique Fernandez, San Bruno, all of Calif.

[73] Assignee: Stauffer Chemical Company, Westport, Conn.

[21] Appl. No.: 940,992

[22] Filed: Dec. 12, 1986

[51] Int. Cl.$^4$ ............................................. A23L 1/035
[52] U.S. Cl. ...................................... 426/33; 426/62; 426/656; 426/52; 426/654
[58] Field of Search .................. 426/33, 7, 61, 62, 44, 426/46, 654, 656, 52; 435/134, 923

[56] References Cited

U.S. PATENT DOCUMENTS 2,316,621  12/1938  Renner ................................. 426/33
4,001,437  1/1977  Jaeggi et al. .......................... 426/34

OTHER PUBLICATIONS

Cirigliano et al. Isolation of a Bidoemulsifier from *Candida lipolytica*, Applied and Environmental Micro. Oct. 1984 vol. 48, No. 4, pp. 747–750.

*Primary Examiner*—Marianne Cintins
*Attorney, Agent, or Firm*—Royal N. Ronning, Jr.; Edwin M. Szala

[57] ABSTRACT

A vegetable oil and mineral salts broth is fermented with an organism to produce a vegetable oil product containing an emulsifier. Fermentation is carried out by forming a fermentation broth of vegetable oil and mineral salts, and optionally yeast extract and then fermenting the broth with *Candia Lipolytica*. The resultant fermented vegetable oil product is used as an emulsifying agent in the food industry.

6 Claims, No Drawings

PRODUCTION OF FERMENTED VEGETABLE OIL PRODUCTS CONTAINING AN EMULSIFIER

FIELD OF THE INVENTION

This invention relates to a method of producing food grade and cosmetic grade emulsifier containing broths by fermention processes.

BACKGROUND OF THE INVENTION

Controlled fermentation of food can be used as a means of improving functionality of food. Vegetable oils are foods which may be an economical source of fermentable substrates. They are widely used as ingredients in manufactured foods. If vegetable oil can be functionalized by fermentation with an organism that produces an emulsifier when grown on these substrates, it is possible to obtain products that may serve the function of an emulsifier or emulsion stabilizer.

Vegetable oils are extracted and refined products derived from various plants such as corn, soybeans, and sunflower plants for example. These oils are consumed as foods themselves or as constituents of other prepared foods.

Applicant has discovered a novel method of producing a functionalized vegetable oil product for use as a food ingredient or any type of product where vegetable oils are acceptable ingredients.

BRIEF DESCRIPTION OF THE INVENTION

The process of this invention provides a method of functionalizing vegetable oil by forming a fermentation broth of the vegetable oil, mineral salts and optionally yeast extract and then fermenting the broth with the organism *Candida lipolytica*.

DETAILED DESCRIPTION OF THE INVENTION

A functionalized vegetable oil having the ability to decrease the surface tension of an oil and water emulsion for use as a food or cosmetic ingredient that may serve as a stabilizer, thickener, or emulsifier, can be produced by fermenting a mixture comprising vegetable oil plus mineral salts and optionally, yeast extract with the organism *Candida lipolytica* to produce a functionalized product containing an emulsifier produced by the organism *Candida lipolytica*.

Any organism that can produce an emulsifier, stabilizer or thickener on the substrate can be useful in the fermentation. The preferred microorganism is *Candida lipolytica* ATCC 20324.

Fermentation of a broth comprising vegetable oil, mineral salts and optionally yeast extract results in stabilizer, thickener or emulsifier formation and functionalization of the vegetable oil so that the oil product can be utilized as a food ingredient. This aerobic fermentation can be carried out preferably in a pH range of 5 to 8, most preferably with the pH maintained in a range from about 5.0 to about 6.0. The fermentation can be carried out at a temperature from about 20° to 35° C., most preferably carried out at a temperature from about 25° to about 30° C.

In the fermentation broth containing the mineral salts listed in Table I the concentration of vegetable oil can range from about 1.0% to about 10.0%, preferably 2% to 5%. The additional yeast extract in the fermentation broth can range from about 0.01% to about 2.0%, preferably from about 0.05% to about 1.0%. Adequate fermentation broth surface tensions of below about 40 mN/m (milliNewtons per meter) are usually reached within 18 to 36 hours. All of the above weight percents are in weight per volume.

Any vegetable oils can be used but the preferred oils are those derived from corn, soybean and sunflower.

By the term "surface tension" is meant the force (tension) of a liquid which makes the surface act as an elastic enveloping membrane which always tends to contract the minimum area. It is expressed as the work required to increase the surface area by one unit and is usually given as milliNewtons per meter (mN/m).

TABLE I

| Composition of Mineral Salts | |
|---|---|
| $(NH_4)_2HPO_4$ | 1.0–10.0 g |
| $K_2HPO_4$ | 0.5–5.0 g |
| $Na_2SO_4$ | 0.1–0.5 g |
| $CaCl_2$ | 0.0–0.05 g |
| $MgSO_4.7H_2O$ | 0.04–0.4 g |
| $FeSO_4.7H_2O$ | 0.002–0.02 g |
| $MnSO_4.H_2O$ | 0.002–0.02 g |
| NaCl | 0.002–0.02 g |

EXAMPLE 1

*Candida lipolytica* ATCC 20324 was grown in baffled 500 ml shake flasks containing 100 ml of mineral salts medium containing per liter: 10 g $(NH_4)_2HPO_4$; 0.5 g $K_2HPO_4$; 0.5 g $Na_2SO_4$; 0.05 g $CaCl$; 0.4 g $MgSO_4.7H_2O$; 0.02 g $FeSO_4.7H_2O$; 0.02 g $MnSO_4.H_2O$; 0.02 g NaCl; 1 g yeast extract; and either 2% or 10% corn oil. The broth containing yeast extract was sterilized by autoclaving for 20 minutes at 121° C. at 15 psig. The corn oil was also sterilized by autoclaving as defined above and added to the broth at the time of use. Flasks were incubated at 30° C., 250 rpm on a rotary shaker for 72 hours. Samples were aseptically withdrawn periodically and the pH and surface tension determined.

Surface tension was measured on a Fisher Autotensiomat ® Model 215. Where indicated, broths were appropriately diluted in 0.02 M Tris® plus 10mM $MgSO_4$ buffer, pH 7.2. The surface tension of this buffer is 68–72 mN/m.

The greatest broth dilution at which the minimum surface tension is reached is the critical micelle dilution (CMD), expressed as the reciprocal of the dilution. At the CMD, surfactant molecules free in solution come into equilibrium with micelles and the concentration of free molecules becomes constant, regardless of increasing total surfactant concentration. Thus, further increase in surfactant concentration do not result in further reductions in surface tension. The greater the dilution at which this occurs the greater the concentration of the surfactant, i.e., the more surfactant produced in the fermentation.

Results are shown in Table 2 for inoculated and uninoculated media.

TABLE 2

Reduction in Surface Tension (ST) by
*C. lipolytica* Growing in Various Media

| Medium Time, hour | Inoculated | | | | Uninoculated Control | | | |
|---|---|---|---|---|---|---|---|---|
| | Broth pH | Surfactant Activity | | | Broth pH | Surfactant Activity | | |
| | | ST[1] @ CMD | CMD[2] | pH @ CMD[2] | | ST[1] @ CMD | CMD[2] | pH @ CMD |
| 2% oil | | | | | | | | |
| 0 | 6.9 | 46 | 0 | 6.9 | 7.0 | 48 | 0 | 7.0 |
| 24 | 6.4 | 29 | 2 | 6.8 | 7.0 | 48 | 0 | 7.0 |
| 48 | 6.2 | 34 | 0.1 | 6.2,6.4 | 7.0 | 48 | 0 | 7.0 |
| 72 | 6.0 | 46 | 0 | 6.0 | 7.0 | 45 | 0 | 7.0 |
| 10% oil | | | | | | | | |
| 0 | 7.0 | 42 | 0 | 7.0 | 7.0 | 44 | 0 | 7.0 |
| 24 | 6.0 | 30,32 | 0,1 | 6.0,6.2 | 6.9 | 38 | 0 | 6.9 |
| 48 | 5.7 | 30 | 2 | 6.8 | 7.0 | 42 | 0 | 7.0 |
| 72 | 5.2 | 29 | 2 | 6.9 | 7.0 | 42 | 0 | 7.0 |

1 = mN/m
2 = 0 Dil = Undiluted broth, 1 = $10^{-1}$, 2 = $10^{-2}$, etc.

At oil concentrations of 2% and 10%, the greatest CMD occurred after 24 hours and 48 hours of incubation, respectively. The CMD was 100 fold greater compared to the uninoculated controls. The surface tension was also lower than in the uninoculated controls.

The surface active broths produced by fermentation techniques of this invention may be concentrated by partial drying, dried or pasteurized and/or dried by lypohilization, spray drying, and other techniques.

The functionalized whey product of this invention can be used as a food or cosmetic ingredient where milk solids and/or whey, and/or vegetable oils, and/or thickeners, and/or emilsifiers, and/or stabilizers are used such as in ice cream, baked goods, salad dressings, foam stabilizers (meringue), puddings, snack foods, hand lotions, shampoos, make-up, etc.

The term "emulsifier" means a substance which makes an emulsion more stable by reducing the surface tension or protecting the droplets with a film.

The term "emulsion" means a fluid consisting of microscopically heterogeneous mixture of two normally immiscible liquid phases, in which one liquid forms minute droplets suspended in the other liquid.

The term "stabilizer" means a substance added to a solution to render it more stable.

The term "thickener" means a substance which when mixed with a fluid increases the viscosity of the fluid.

The term "functionality" means to impart a new function to a fermetable substrate material by the action of the microorganism. The entire fermentation broth, including the microorganism, is utilized without seperation for the purpose of the new function as a naturally produced material exhibit the function.

What is claimed is:

1. A process for producing a fermented functionalized vegetable oil product containing an emulsifier consisting essentially of:
   (a) forming a fermentation broth of from about 1 to about 10% by wt/vol. vegetable oil and a mineral salts medium; and
   (b) fermenting the broth with an effective amount of the organism, *Candida lipolytica* at a time and a temperature sufficient to produce a functionalized vegetable oil product containing an emulsifier produced by the organism wherein said mineral salts medium is an aqueous solution consisting of 1 10gm/l of $(NH_4)_2HPO_4$, 0.5–5gm/l $K_2HPO_4$, 0.1–0.5 gm/l $Na_2SO_4$, 0.0–0.05gm/l $CaCl_2$, 0.04–0.4gm/l $MgSO_4.7H_2O$, 0.002–0.02 gm/l $FeSO_4.7H_2O$, 0.002–0.02gm/l $MnSO_4.H_2O$, and 0.002–0.02gm/l NaCl.

2. The process of claim 1 wherein the fermentation broth also contains from about 0.01 to about 2.0% wt/vol. yeast extract.

3. The process of claim 1 wherein the vegetable oil concentration ranges from about 2% to about 5% by wt/vol.

4. A fermented functionalized vegetable oil containing an emulsifier emulsification comprising a fermented vegetable oil produced by the processs of
   (a) forming a fermentation broth of from about 1 to about 10% by wt/vol. unhydrolyzed vegetable oil and a mineral salts medium; and
   (b) fermenting the broth with an effective amount of the organism *Candida lipolytica* at a time and a temperature sufficient to produce a functionalized vegetable oil product containing an emulsifier produced by the organism wherein said mineral salts medium is an aqueous solution consisting of 1–10 gm/l of $(NH_4)_2HPO_4$, 0.5–5 gm/l $K_2HPO_4$, 0.1–0.5 gm/l $Na_2SO_4$, 0.0–0.05 gm/l $CaCl_2$, 0.04–0.4 gm/l $MgSO_4.7H_2O$, 0.002–0.02 gm/l $FeSO_4.7H_2O$, 0.002–0.02 gm/l $MnSO_4.H_2O$, and 0.002–0.02 gm/l NaCl.

5. A concentrated product of claim 4.

6. A dried product of claim 4.

* * * * *